United States Patent [19]
Garrett

[11] Patent Number: 4,973,314
[45] Date of Patent: Nov. 27, 1990

[54] COMBINED DRESSING AND RETAINER FOR SURGICALLY IMPLANTED CATHETER

[76] Inventor: Susan Garrett, 167 Cherry St. - No. 233, Milford, Conn. 06460

[21] Appl. No.: 332,353

[22] Filed: Mar. 31, 1989

[51] Int. Cl.⁵ .............................................. A61M 5/32
[52] U.S. Cl. ............................. 604/180; 128/DIG. 26
[58] Field of Search .............. 604/174, 175, 176, 179, 604/, 180, 304, 305, 307, 313; 120/112.1, DIG. 26, 155, 171

[56] References Cited

U.S. PATENT DOCUMENTS

| | | | |
|---|---|---|---|
| 3,138,158 | 6/1964 | Gordon et al. | 604/180 |
| 3,918,446 | 11/1975 | Buttaravoli | 604/180 |
| 4,324,237 | 4/1982 | Buttaravoli | 604/180 |
| 4,490,141 | 12/1984 | Lacko et al. | 604/180 |
| 4,578,062 | 3/1986 | Schneider | 640/174 |
| 4,666,432 | 5/1987 | McNeish et al. | 604/174 |
| 4,907,579 | 3/1990 | Kum | 604/304 |

FOREIGN PATENT DOCUMENTS

| | | | |
|---|---|---|---|
| 2451022 | 10/1974 | Fed. Rep. of Germany | 604/180 |
| 2211417 | 7/1989 | United Kingdom | 604/180 |

Primary Examiner—C. Fred Rosenbaum
Assistant Examiner—Kathleen A. Daley
Attorney, Agent, or Firm—Brooks Haidt Haffner & Delahunty

[57] ABSTRACT

A one-piece gauze dressing is provided with joined portions, one smaller than the other, and with adhesive stripes to secure the smaller portion to a human body over an extending implanted catheter tube. The second or larger portion can be folded over the catheter tube that has been coiled whereupon the second portion is adhesively joined to the first portion and to the skin of the patient.

22 Claims, 1 Drawing Sheet

COMBINED DRESSING AND RETAINER FOR SURGICALLY IMPLANTED CATHETER

BACKGROUND OF THE INVENTION

The present invention relates to sterile dressings of the type used to cover the entry site through which a surgically embedded catheter enters the body. It also relates to devices for retaining the free end of the embedded catheter in a compact protected environment when the catheter is not being used.

In U.S. Pat. No. 4,666,432 issued May 19, 1987 to McNeish et al. there is described a catheter retaining means for use with a surgically implanted catheter having an external tubing portion with a free end extending from an exit site on the body. The retaining means comprises a band of flexible material for being received about the body and over the exit site of the implanted catheter for protecting the site of the body and securely retaining in position proximate to the body the external tubing portion as it extends from the exit site. The band has an opening and a pocket overlying the opening for receiving into the pocket through the opening at least a part of the external tubing portion and its free end for storage therein, the pocket allowing the removal therefrom of the free end and part of the external tubing portion of the catheter for placing it in use. This retaining means is constructed of launderable fabric and is not intended to function as a dressing for the exit site. Instead, as explained in the patent, 2-inch square sterile pads must be applied over the exit site and held in place by strips of ½ inch wide tape. Obviously, the patented device can not readily be provided in a universal size and configuration to fit all age groups of both sexes over various parts of the body.

In U.S. Pat. No. 4,059,105, issued on Nov. 22, 1977 to Cutruzzula et al. there is described a cannula securing device in the form of a generally T-shaped lamina having a wide head portion foldable about a lateral weakening to be superimposed on a narrow body portion which includes an elongated opening for permitting viewing of a portion of the skin of a patient. Adhesive is provided on one side of the narrow body portion and on the opposite side of the wide head portion for securing the lamina to a common surface.

There is no provision for covering the entry site of the cannula apart from the overlapping of the wide head portion. It is intended strictly as a retaining device and not as a dressing for the entry site.

Implanted catheters are used in connection with various medical procedures. One use is in chemotherapy treatment of cancer. An example is the Hickman Broviac catheter which is surgically introduced through an opening into a blood vessel. Typically the site is in the upper chest near the heart but it could be located in the thigh or other suitable part of the body. To prevent infection at the entry site the area must be kept clean and it is standard practice to keep it covered with a sterile dressing which is changed daily. Normal use of the catheter is intermittent and when not in use it has been the practice to coil the exposed end of the catheter and tape it to the body.

SUMMARY OF THE INVENTION

It is therefore an object of the present invention to provide a simple expendable dressing structure that also serves to retain the free end of the catheter when not in use.

Another object of the present invention is to provide an article of the aforementioned character which is inexpensive to produce.

Yet another object is to provide a sterile dressing that can be changed as frequently as desired and which, at the same time, provides for compact retention of the free end of the catheter.

A further object of the present invention is to provide a universal dressing that can be used optionally as either an occlusive or non-occlusive dressing where an occlusive dressing excludes air from the entry site while a non-occlusive dressing does not.

Other objects will occur to those skilled in the subject art after reading the present disclosure.

In accordance with an aspect of the present invention there is provided a combined dressing and retainer for topical use with a surgically implanted catheter for protecting the entry site and selectively housing the free end of the catheter. The dressing comprises a panel of wound dressing material divided into first and second portions joined at a straight fold line. The two portions are geometrically similar with said first portion being smaller than said second portion, and said first portion having an aperture through which can be passed the exposed end of an implanted catheter. A first layer of pressure sensitive adhesive is provided on one side of the panel within the confines of the first portion in a stripe between the aperture and said fold line. A second layer of pressure sensitive adhesive is provided on the opposite side of the panel in a stripe bordering the entire perimeter of said second portion with the exception of said fold line. The second stripe is wider than that region of said second portion which extends beyond the boundary of said first portion whenever said second portion is folded along said fold line over said first portion for adhesively joining said second portion to said first portion around the perimeter of said first portion when so folded thereover while simultaneously adhesively joining said second portion to the skin of a patient.

BRIEF DESCRIPTION OF THE DRAWINGS

The invention will be better understood after reading the following detailed description of the presently preferred embodiment thereof with reference to the appended drawings in which:

FIG. 6 is a view similar to FIGS. 4 and 5 showing the combined dressing and retainer completely in place protecting the entry site and retaining the free end of the catheter.

The same reference numerals are used throughout the drawings to designate the same or similar parts.

DETAILED DESCRIPTION OF THE PRESENTLY PREFERRED EMBODIMENTS

Figure 1:
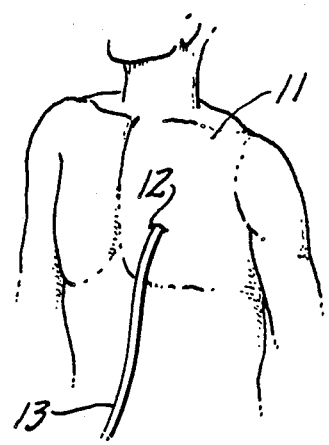
FIG. 1 is a fragmentary sketch in perspective showing a catheter implanted in a torso for the purpose of illustrating the use of the present invention.

Referring to FIG. 1, there is shown merely by way of example, the torso 10 of an individual in whose chest 11 a catheter has been implanted surgically through a surgical incision 12. The construction of the catheter and its insertion will follow well known procedures, the details of which form no part of the present invention. What is important is that the catheter exits the chest from the entry site or incision 12, and its free or exposed end 13 dangles loose unless restrained in some fashion. Since the incision is an open wound it must be kept dressed and protected. Heretofore, gauze dressings were placed around the site and held in place by suitable adhesive tape. Such dressings are typically changed at least daily.

Figure 2:
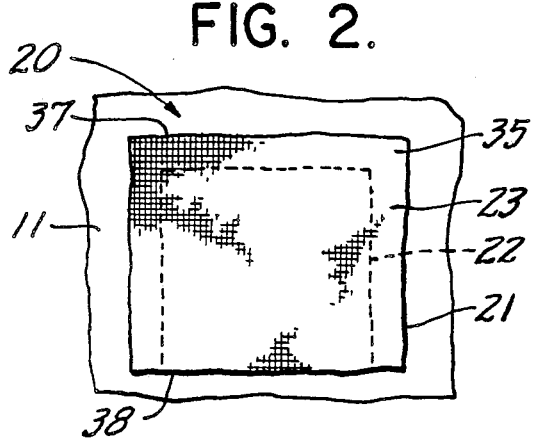
FIG. 2 is a top plan view of a combined dressing and retainer embodying the present invention.
Figure 2:
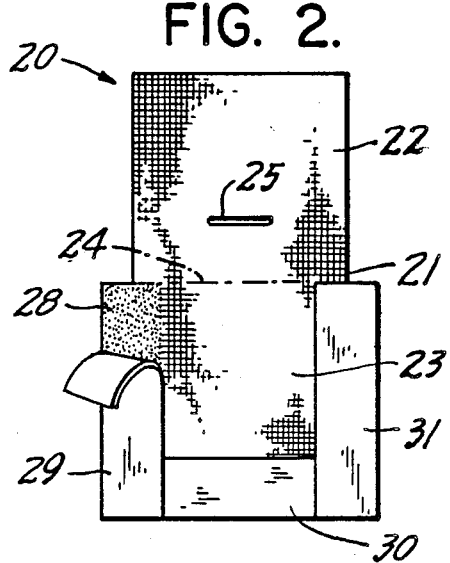
Figure 3:
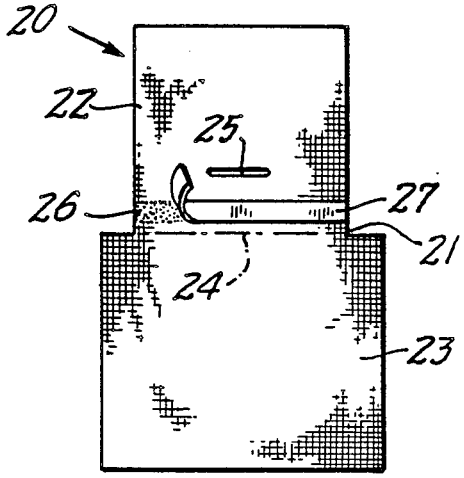
FIG. 3 is a bottom plan view of the combined dressing and retainer illustrated in FIG. 2.

Turning now to FIGS. 2 and 3, there is shown designated generally by the reference numeral 20, an embodiment of the present invention. The dressing 20 consists of a panel 21 of wound dressing material, usually layers of gauze, divided into first and second portions 22 and 23, respectively. The portions 22 and 23 are joined at a straight fold line 24. As clearly shown, the two portions 22 and 23 are geometrically similar, in this instance both are square. They could be rectangular or circular or any other suitable shape. The portion 22 is smaller than the portion 23 and contains an aperture 25 for a purpose to be described below.

Referring to FIG. 3, the panel 21 will be seen to have a layer of pressure sensitive adhesive 26 extending across the width of portion 22 within its boundaries or confines in a stripe between the aperture 25 and the fold line 24 paralleling the fold line 24. As seen in FIG. 3, the adhesive stripe 26 is covered and protected by a strip 27 of suitable release paper. The paper 27 is shown partially peeled back in FIG. 3 merely for purpose of illustration.

On the opposite side of panel 21 as shown in FIG. 2, another layer of pressure sensitive adhesive 28 is provided in a stripe bordering the entire perimeter of the portion 23 with the exception of the fold line 24. The stripe 28 is normally protected by strips of release paper 29, 30 and 31, the strip 29 being shown peeled back for purpose of illustration only. Also, the adhesive stripe 28 will be observed as wider than that part of the border region of the portion 23 that exceeds the dimensions of the portion 22.

Figure 4:
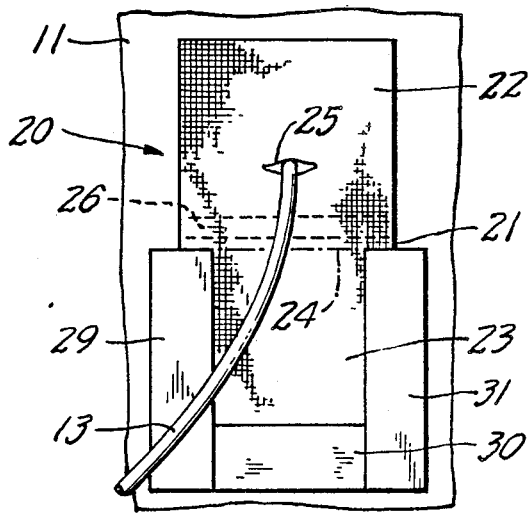
FIG. 4 illustrates the initial step in placing the combined dressing and retainer of FIGS. 1 and 2 in position against the body over the projecting catheter.
Figure 5:
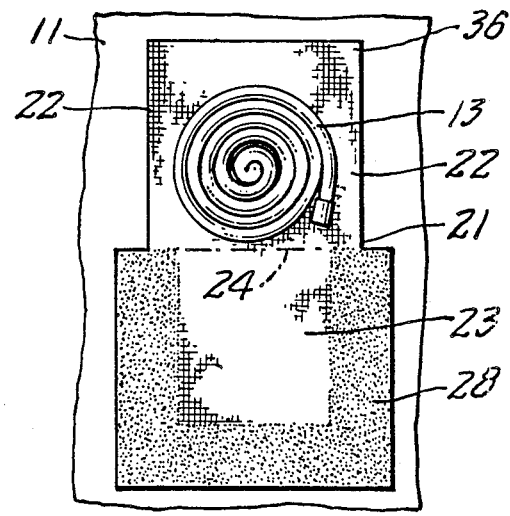
FIG. 5 is a view similar to FIG. 4 but showing the catheter coiled preparatory to encasing it in the combined dressing and retainer.

When it is desired to apply the dressing-retainer 20, the free end 13 of the catheter is passed through the aperture 25 from the side shown in FIG. 3 so that the portion 22 can be placed against the skin of the patient as illustrated in FIG. 4. The release paper 27 is removed and portion 22 is secured to the body 11 by adhesive 26. Next, the catheter end 13 is coiled as shown in FIG. 5, the release papers 29, 30 and 31 are removed, and the portion 23 is folded along line 24 over the coiled catheter 13 and over portion 22.

The completed application of the dressing is shown in FIG. 6. It should now be appreciated that the adhesive stripe 28 is wider than that part or region of portion 23 which extends beyond the boundary of portion 22 when the portion 23 is folded over portion 22. Thus, adhesive 28 joins the portion 23 to portion 22 around the perimeter of portion 22 while simultaneously adhesively joining portion 23 to the skin of the patient. This construction is particularly advantageous because if the attending medical personnel desire to inspect the entry site they can merely peel back one corner of the dressing, say the corner 35. Bearing in mind that the adhesive stripe 28 secures panel portions 22 and 23 together, when the corner of stripe 28 is peeled away from the patient's skin, the corner 36 (see FIG. 5) of portion 22 will peel back along with portion 23 to permit visual access to the site 12 without releasing the coiled end of catheter 13.

A typical embodiment for adult use can be constructed with the following dimensions. Portion 22 can be 4" wide with 4" long sides, while portion 23 is 5" wide with 4½" long sides. Adhesive stripe 26 is approximately ⅜" wide, while adhesive stripe 28 is about 1" wide. Slit 25 can be ⅞" long and located about 1" from the fold line 24, centered between the two side edges. It is to be understood, however, that the mentioned dimensions are only exemplary and can be varied as desired while the structure retains its overall function. For example, for pediatric use, portion 22 might be as small as 2" square or smaller, while portion 23 is 3" wide with long sides measuring about 2½". The adhesive stripes can be the same width as in the adult embodiment or slightly narrower.

While in the described embodiment the externally overlapping portion 23 is composed of layers of gauze throughout, it is contemplated that at least a central window section of portion 23 can be replaced with a layer of transparent material so that a physician or other medical attendant can observe the condition of the catheter free end 13 and can also observe the condition of the inner portion 22. The condition of the latter can reveal abnormal discharge from the entry site requiring treatment or the need for changing the dressing, all without the need to pull back the portion 23 with its accompanying irritation of the patient's skin caused by peeling or separating the adhesive layer 28 from the skin of the patient.

With the constructions described above, the entry site 12 is covered by a porous dressing permitting air to reach the site 12 even though the entire perimeter of the dressing is adhesively joined to the skin of the patient. However, under certain circumstances it may be desirable to exclude air from the site 12. For this purpose at least the portion 23, and preferably the entire dressing 21, can be impregnated with a suitable polymeric material; or a layer of polymeric film can be laminated with the gauze layers, to render the dressing impermeable to air. Now, as explained below, the physician or medical attendant has the option of excluding air or not, depending upon the circumstances.

Assuming that the panel 21 is constructed with air impermeable material as mentioned above, if, for example, the release paper strip 30 is not removed, the upper edge 37 of the dressing (see FIG. 6) will not be sealed to the chest of the patient and air will have direct access at edge 37 under the portion 22. On the other hand, if paper 30 is removed along with strips 29 and 31, all of the edges of portion 22 will be covered and sealed to the skin. With portion 23 being impervious, no air can reach the site 12.

Alternatively, assuming it is not required to hold the dressing in place, the release strip 27 can be left in place. Now, air can enter under the lower edge 38 (see FIG. 6) of the dressing to reach the site 12.

Having described the present invention with reference to the presently preferred embodiments thereof, it is to be understood that various changes can be made as will be apparent to those skilled in the subject art without departing from the true spirit of the invention as defined in the appended claims.

What is claimed is:

1. A combined dressing and retainer for topical use with a surgically implanted catheter for protecting the entry site and selectively housing the free end of the catheter, said dressing comprising a panel of wound dressing material divided into first and second portions joined at a straight fold line, said two portions being geometrically similar but with said first portion of smaller size than said second portion, said portions and fold line being located and related one to the other such that when said second portion is folded along said fold line over said first portion said second portion will overlap and extend laterally beyond said first portion around the entire perimeter of said first portion with the exception of said fold line, said first portion having an aperture through which can be passed the exposed end of an implanted catheter, a first layer of pressure sensitive adhesive on one side of said panel within the confines of said first portion in a stripe located between said aperture and said fold line, and a second layer of pressure sensitive adhesive on the opposite side of said panel in a stripe bordering the entire perimeter of said second portion with the exception of said fold line, said second stripe being wider than the region of said second portion which extends beyond the boundary of said first portion whenever said second portion is folded along said fold line over said first portion for adhesively joining said second portion to said first portion around the perimeter of said first portion when so folded thereover while simultaneously adhesively joining said second portion to the skin of a patient.

2. A combined dressing and retainer according to claim 1, wherein said panel comprises sterile gauze.

3. A combined dressing and retainer according to claim 2, wherein said panel portions have a rectilinear shape.

4. A combined dressing and retainer according to claim 3, wherein said panel portions are substantially square.

5. A combined dressing and retainer according to claim 4, wherein said panel portions measure at least 2" by 2".

6. A combined dressing and retainer according to claim 5, wherein said second panel portion when folded over said first panel portion extends beyond the latter on each of three sides by about one half inch.

7. A combined dressing and retainer according to claim 6, wherein said second stripe of adhesive is about 1" wide.

8. A combined dressing and retainer according to claim 2, wherein said second panel portion when folded over said first panel portion extends beyond the latter on each of three sides by about one half inch.

9. A combined dressing and retainer according to claim 8, wherein said second stripe of adhesive is about 1" wide.

10. A combined dressing and retainer according to claim 3, wherein said second panel portion when folded over said first panel portion extends beyond the latter on each of three sides by about one half inch.

11. A combined dressing and retainer according to claim 10, wherein said second stripe of adhesive is about 1" wide.

12. A combined dressing and retainer according to claim 4, wherein said second panel portion when folded over said first panel portion extends beyond the latter on each of three sides by about one half inch.

13. A combined dressing and retainer according to claim 12, wherein said second stripe of adhesive is about 1" wide.

14. A combined dressing and retainer according to claim 13, wherein said first portion is about four inches square.

15. A combined dressing and retainer according to claim 1, wherein said first layer of pressure sensitive adhesive is arranged in a stripe paralleling said fold line coextensive therewith and adjacent thereto.

16. A combined dressing and retainer according to claim 15, wherein said panel comprises sterile gauze.

17. A combined dressing and retainer according to claim 16, wherein said panel portions have a rectilinear shape.

18. A combined dressing and retainer according to claim 17, wherein said panel portions are substantially square.

19. A combined dressing and retainer according to claim 18, wherein said panel portions measure at least 2" by 2".

20. A combined dressing and retainer according to claim 19, wherein said second panel portion when folded over said first panel portion extends beyond the latter on each of three sides by about one half inch.

21. A combined dressing and retainer according to claim 1, wherein at least said second portion of said panel is air impermeable.

22. A combined dressing and retainer according to claim 21, wherein said entire panel is air impermeable.

* * * * *